(12) United States Patent
Minamimoto et al.

(10) Patent No.: US 12,201,994 B2
(45) Date of Patent: Jan. 21, 2025

(54) MAGNETIC PARTICLE MANIPULATING APPARATUS

(71) Applicant: SHIMADZU CORPORATION, Kyoto (JP)

(72) Inventors: Ayaka Minamimoto, Kyoto (JP); Masamitsu Shikata, Kyoto (JP); Nobuhiro Hanafusa, Kyoto (JP); Akira Muramatsu, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 727 days.

(21) Appl. No.: 17/493,344

(22) Filed: Oct. 4, 2021

(65) Prior Publication Data

US 2023/0109542 A1  Apr. 6, 2023

(51) Int. Cl.
*B03C 1/28* (2006.01)
*B01L 9/06* (2006.01)
*B03C 1/01* (2006.01)
*B03C 1/033* (2006.01)
*B03C 1/12* (2006.01)
*B03C 1/30* (2006.01)
*C12N 15/10* (2006.01)

(52) U.S. Cl.
CPC ............ *B03C 1/288* (2013.01); *B01L 9/06* (2013.01); *B03C 1/01* (2013.01); *B03C 1/0332* (2013.01); *B03C 1/12* (2013.01); *C12N 15/1013* (2013.01); *B01L 2200/0631* (2013.01); *B03C 2201/18* (2013.01)

(58) Field of Classification Search
CPC ......... B03C 1/288; B03C 1/01; B03C 1/0332; B03C 1/12; B03C 2201/18; B01L 9/06; B01L 2200/0631; C12N 15/1013
See application file for complete search history.

(56) References Cited

U.S. PATENT DOCUMENTS

| 2015/0185120 A1* | 7/2015 | Nagai ............ B01L 9/06 422/549 |
| 2016/0180998 A1 | 6/2016 | Kanai et al. |
| 2017/0152509 A1 | 6/2017 | Ohashi |

FOREIGN PATENT DOCUMENTS

| JP | 2003-075457 A | 3/2003 |
| JP | 2005-013413 A | 1/2005 |

(Continued)

OTHER PUBLICATIONS

Jun. 7, 2022, Japanese Office Action issued for related JP Application No. 2019-070754.

*Primary Examiner* — Jill A Warden
*Assistant Examiner* — Michael Stanley Gzybowski
(74) *Attorney, Agent, or Firm* — Paratus Law Group, PLLC

(57) ABSTRACT

A magnetic particle manipulating apparatus includes a magnetic force source moving mechanism, an operation controller configured to control operation of the magnetic source moving mechanism, an openable cover for covering the device holder, a pressing mechanism provided on the cover to press the tubular device held by the device holder when the cover is closed so that warpage of the tubular device is corrected, an open/close state detector provided so as to detect an open/close state of the cover. The operation controller is configured to execute the processing operation only in a case where the open/close state detector detects that the cover is closed.

4 Claims, 6 Drawing Sheets

(56) References Cited

FOREIGN PATENT DOCUMENTS

| | | |
|---|---|---|
| JP | 2014-083041 A | 5/2014 |
| JP | 2014-221111 A | 11/2014 |
| JP | 2016-117032 A | 6/2016 |
| WO | WO 2015/177933 A1 | 11/2015 |

* cited by examiner

MAGNETIC PARTICLE MANIPULATING APPARATUS

TECHNICAL FIELD

The present invention relates to a magnetic particle manipulating apparatus for manipulating a magnetic particle capturing a target substance in a tubular device in which layers of treatment liquid for performing treatment such as separation or purification of the target substance are layered with a gel layer interposed between them.

BACKGROUND ART

It has been proposed and carried out to separate and purify a target substance such as a nucleic acid using a tubular device in which a plurality of treatment liquid layers formed by treatment liquid such as a solution/fixing solution, a cleaning solution, and an eluate are layered with a gel layer interposed between them (see Patent Document 1).

The separation and purification of a target substance using such a tubular device are performed by introducing a magnetic particle capturing the target substance into the tubular device and manipulating the magnetic particle in the tubular device with a magnet outside the tubular device. When the treatment liquid layer is a cleaning solution, the magnet is reciprocated at a high speed along the longitudinal direction of the tubular device so that high-speed stirring motion by the magnetic particle is performed in the treatment liquid layer.

In order to automatically perform the separation and purification of a target substance using a magnetic particle as described above, a magnetic particle manipulating apparatus that automatically moves a magnetic force source for manipulating a magnetic particle in the tubular device in the longitudinal direction of the tubular device has been proposed (see Patent Document 2).

In the magnetic particle manipulating apparatus as described above, it is necessary to move the magnetic force source in the longitudinal direction of the tubular device in a state where the distance between the tubular device and the magnetic force source is kept constant. On the other hand, the tubular device is generally composed of a tube made from resin, and there is also a tubular device that is warped. In a case where the tubular device is warped, when the magnetic force source is moved in a uniaxial direction along the longitudinal direction of the tubular device, the distance between the magnetic force source and the tubular device changes depending on a position of the magnetic force source, and there is possibility that some of magnetic particles in the tubular device do not follow the magnetic force source, and the magnetic particles in the tubular device cannot be manipulated accurately. For this reason, Patent Document 2 proposes to correct the warpage of the tubular device by pressing the tubular device in a direction perpendicular to the longitudinal direction of the tubular device.

PRIOR ART DOCUMENTS

Patent Documents

Patent Document 1: WO2015/177933A1

Patent Document 2: Japanese Patent Laid-open Publication No. 2016-117032

SUMMARY OF THE INVENTION

Problems to be Solved by the Invention

A mechanism for pressing the tubular device to correct warpage of the tubular device may be provided on an openable cover that covers a device holder that holds the tubular device. In this case, the warpage of the tubular device is corrected only by causing the device holder to hold the tubular device and closing the cover, and the constancy of the distance between the magnetic force source and the tubular device is ensured. Conversely, in a case where the cover is open, the constancy of the distance between the magnetic force source and the tubular device is not ensured. Therefore, when the processing of manipulating the magnetic source is performed in a state where the cover is open, the predetermined processing for a target substance is not ensured to be accurately performed.

In view of the above, an object of the present invention is to prevent execution of processing of manipulating the magnetic force source in a state where the constancy of the distance between the magnetic force source and the tubular device is not ensured.

Solutions to the Problems

In a magnetic particle manipulating apparatus according to the present invention, a tubular device in which a plurality of treatment liquid layers formed by treatment liquid for performing processing on a target substance are layered in a longitudinal direction in a state where a gel layer interposed between them, the tubular device being loaded inside with a magnetic particle capturing the target substance is used. The magnetic particle manipulating apparatus includes at least one device holder for holding the tubular device, a magnetic force source for manipulating the magnetic particle from outside of the tubular device by applying a magnetic force to the magnetic particle in the tubular device held by the device holder, a magnetic source moving mechanism that moves the magnetic source in a longitudinal direction of the tubular device at a position close to the tubular device held by the device holder, an operation controller configured to execute processing operation of moving the magnetic particle in the tubular device to each of the treatment liquid layers sequentially by controlling operation of the magnetic source moving mechanism, an openable cover that covers the device holder, a pressing mechanism provided on the cover to press the tubular device held by the device holder toward the magnetic force source when the cover is closed so that warpage of the tubular device is corrected, and an open/close state detector that detects an open/close state of the cover. Then, the operation controller is configured to execute the processing operation only in a case where the open/close state detector detects that the cover is closed.

That is, the magnetic particle manipulating apparatus according to the present invention is configured such that the openable cover for covering the device holder is provided with the pressing mechanism that presses the tubular device in a state where the cover is closed to correct warpage of the tubular device, and the processing operation is not executed in a state where the cover is open, that is, in a state where the warpage of the tubular device is not corrected.

In a preferred embodiment of the magnetic particle manipulating apparatus of the present invention, the operation controller is configured to stop the operation of the magnetic source moving mechanism to stop the processing operation when the open/close state detector detects that the cover is open while the processing operation is executed.

Further, in a preferred embodiment of the magnetic particle manipulating apparatus of the present invention, the operation controller is configured not to execute the processing operation when the open/close state detector detects that the cover is open at the time when an instruction to start the processing operation is input.

Further, in the magnetic particle manipulating apparatus of the present invention, two or more of the device holders may be provided. In that case, a magnetic force source corresponding to each of the device holders is provided. A plurality of the magnetic sources corresponding to the device holders can be moved by a common magnetic source moving mechanism. However, in this case, the magnetic source operates in the device holder in which the tubular device is not installed even if only some of the device holders are used. Further, in the device holder in which the tubular device is not installed, the magnetic force source is in a state of being exposed. For this reason, when the magnetic force source is operated in a state in which the cover is open, there is a possibility that a finger of the user or the like touches the operating magnetic force source. However, in the present invention, since the processing operation is not performed when the cover is open, it is possible to prevent a finger of the user or the like from touching the operating magnetic source.

Effects of the Invention

The magnetic particle manipulating apparatus according to the present invention is configured so that the processing operation is not executed in a state where the cover is open, that is, in a state where warpage of the tubular device is not corrected. Accordingly, it is possible to prevent the processing of operating the magnetic force source from being executed in a state where the constancy of the distance between the magnetic force source and the tubular device is not ensured.

EMBODIMENTS OF THE INVENTION

Hereinafter, an embodiment of a magnetic particle manipulating apparatus will be described with reference to the drawings.

Figure 6:
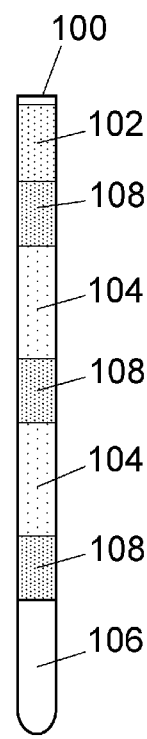
FIG. 6 is a diagram illustrating an example of the tubular device used in the embodiment.

First, an example of a tubular device used in the magnetic particle manipulating apparatus of the embodiment will be described with reference to FIG. 6.

In a tubular device 100, a sample layer 102, a gel layer 108, a treatment liquid layer 104, a gel layer 108, a treatment liquid layer 104, a gel layer 108, and an eluate layer 106 are layered in the longitudinal direction from one end side in the tube.

A sample constituting the sample layer 102 includes a magnetic particle capturing a target substance such as a nucleic acid. The treatment liquid layer 104 is formed by treatment liquid for treating the target substance captured by the magnetic particle. Examples of the treatment liquid include a cleaning solution for removing an impurity substance from the target substance captured by the magnetic particle. An eluate constituting the eluate layer 106 is for dissolving a target substance for which treatment such as separation and purification is performed through the treatment liquid layer 104, and, for example, pure water can be used as the eluate.

Figure 1:
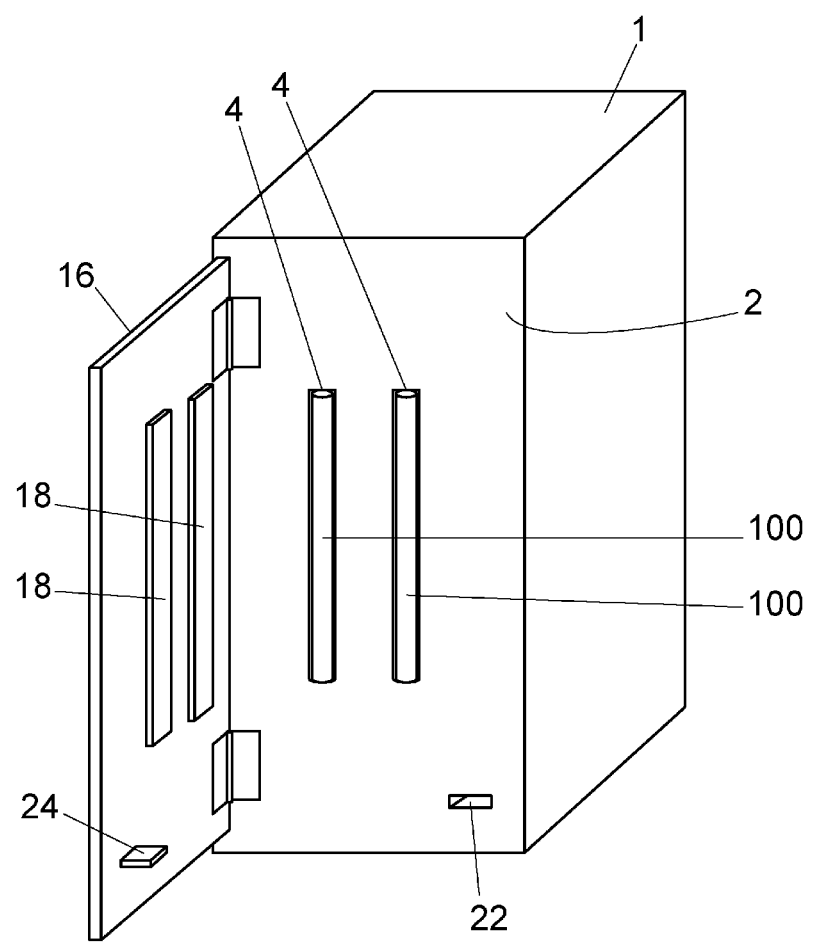
FIG. 1 is a perspective view illustrating an embodiment of a magnetic particle manipulating apparatus.
Figure 2:
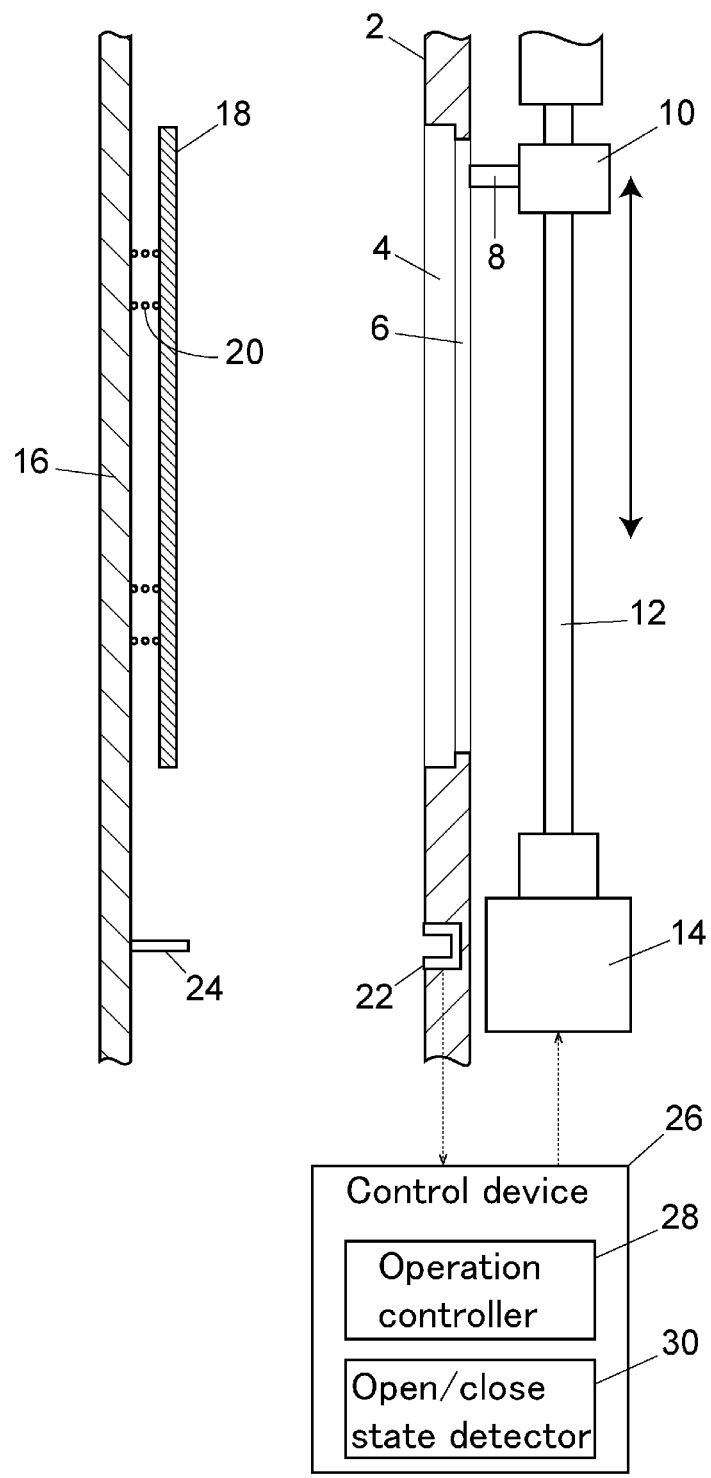
FIG. 2 is a schematic configuration diagram of the embodiment.
Figure 3:
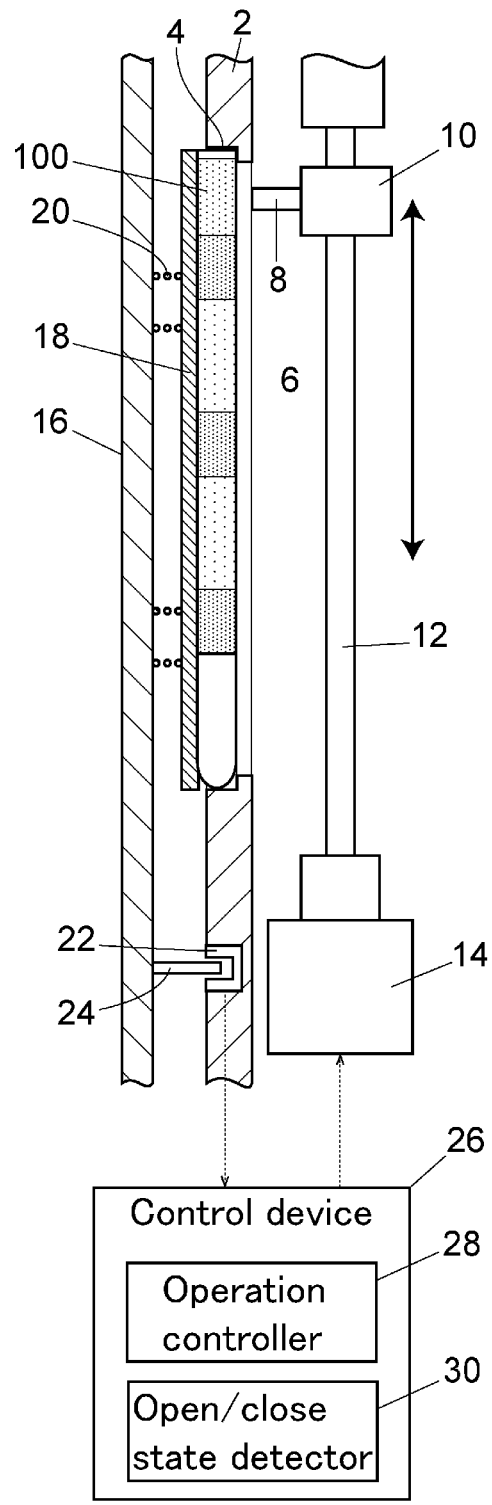
FIG. 3 is a schematic configuration diagram illustrating a state in which a tubular device is held by a device holder of the embodiment.

Next, an embodiment of the magnetic particle manipulating apparatus will be described with reference to FIGS. 1, 2, and 3.

The magnetic particle manipulating apparatus is provided with a recess 4 for fitting the tubular device 100 into a front panel 2 of a housing 1. The recess 4 constitutes a device holder for holding the tubular device 100. In the present embodiment, two of the recesses 4 are provided on the front surface 2. However, the present invention is not limited to this configuration, and one or three or more of the recesses 4 may be provided.

A magnetic force source 8, a holding block 10, a ball screw 12, and a stepping motor 14 are provided inside the housing 1 and behind the front panel 2. The magnetic force source 8 generates a magnetic force for manipulating the magnetic particle in the tubular device 100, and is realized by, for example, a permanent magnet. The ball screw 12 is provided in parallel with the longitudinal direction of the tubular device 100 fitted to the recess 4 on the front panel 2, and is rotated by the stepping motor 14. The holding block 10 is screwed with the ball screw 12, and moves in the axial direction of the ball screw 12 as the ball screw 12 rotates. The holding block 10, the ball screw 12, and the stepping motor 14 constitute a magnetic force source moving mechanism for moving the magnetic force source 8 in the longitudinal direction of the tubular device 100.

An opening 6 for exposing the magnetic force source 8 to the tubular device 100 fitted to the recess 4 is provided on a bottom surface of the recess 4 of the front panel 2. The magnetic force source 8 is held in the vicinity of the tubular device 100 fitted to the recess by the holding block 10, and moves in the longitudinal direction of the tubular device 100 along with the movement of the holding block 10 in the axial direction of the ball screw 12. The magnetic particle in the tubular device 100 follows a motion of the magnetic force source 8 by the action of a magnetic force from the magnetic force source 8, and move in the longitudinal direction in the tubular device 100.

An openable cover 16 is attached to the front panel 2. The cover 16 is provided so as to cover a region where the recess 4 is provided when closed. A pressing plate 18 for pressing the tubular device 100 fitted to the recess 4 toward the magnetic force source 8 side when the cover 16 is closed is attached to the inner side of the cover 16 by an elastic member 20. When the cover 16 is closed, the pressing plate 18 abuts on the tubular device 100 and is biased toward the tubular device 100 side by the elastic member 20, so that warpage of the tubular device 100 is corrected. The pressing plate 18 and the elastic member 20 constitute a pressing mechanism for pressing the tubular device 100 to correct warpage. Although not illustrated, the front panel 2 and the cover 16 are provided with a lock mechanism for maintaining the cover 16 in a closed state.

A microsensor 22 and a sensor dog 24 for detecting an open/close state of the cover 16 are provided on inner surfaces of the front panel 2 and the cover 16. In FIGS. 1 to 3, the microsensor 22 is provided on the front panel 2 side and the sensor dog 24 is provided on the cover 16 side. However, conversely, the sensor dog 24 may be provided on the front panel 2 side and the microsensor 22 may be provided on the cover 16 side.

The magnetic particle manipulating apparatus includes a control device 26 for controlling operation of the stepping motor 14. The control device 26 can be realized by an electronic circuit including an arithmetic element and a storage medium. The control device 26 includes an operation controller 28 and an open/close state detector 30. The operation controller 28 and the open/close state detector 30 are functions implemented by an arithmetic element executing a program.

The operation controller 28 is configured to control the operation of the stepping motor 14 to move the magnetic force source 8 in the longitudinal direction of the tubular device 100, move the magnetic particle in the tubular device 100 from the sample layer 102 to the treatment liquid layers 104 and the eluate layer 106 sequentially, and execute predetermined processing operation for a target substance captured by the magnetic particle. Purification treatment of the target substance is performed by reciprocating the magnetic particle at a high speed in the longitudinal direction of the tubular device 100 in the treatment liquid layer 104.

The open/close state detector 30 is configured to detect an open/close state of the cover 16 on the basis of a signal from the microsensor 22.

The operation controller 28 is further configured to execute the processing operation on the target substance only in a case where the open/close state detector 30 detects that the cover 16 is closed. Specifically, even in a case where an instruction to start the processing operation is input by the user, the processing operation is not started in a case where the cover 16 is open. Furthermore, when the cover 16 is opened during the execution of the processing operation, the processing operation is stopped.

Figure 4:
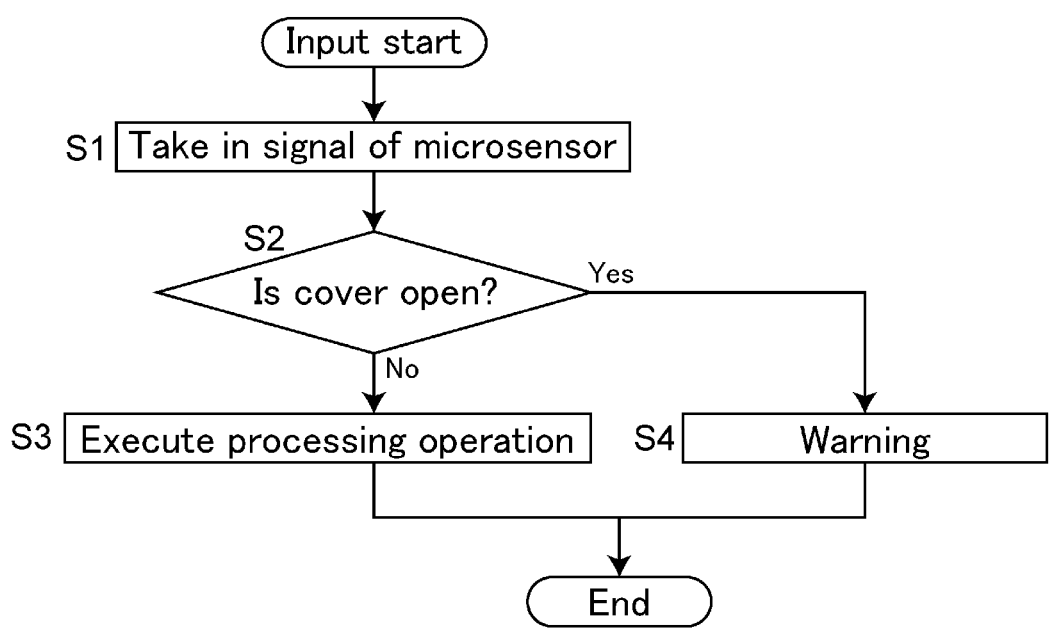
FIG. 4 is a flowchart for explaining operation when start of processing operation of the embodiment is input.

Operation when the instruction to start the processing operation is input will be described with reference to FIG. 3 and the flowchart of FIG. 4.

When the instruction to start the processing operation is input, the open/close state detector 30 checks the open/close state of the cover 16 based on a signal of the microsensor 22 (Steps S1 and S2). In a case where the cover 16 is closed, the operation controller 28 starts the processing operation (Step S3). In contrast, in a case where the cover 16 is open, a warning for allowing the user to recognize that the cover 16 is open is issued (Step S4), and the processing operation waits without being started.

Figure 5:
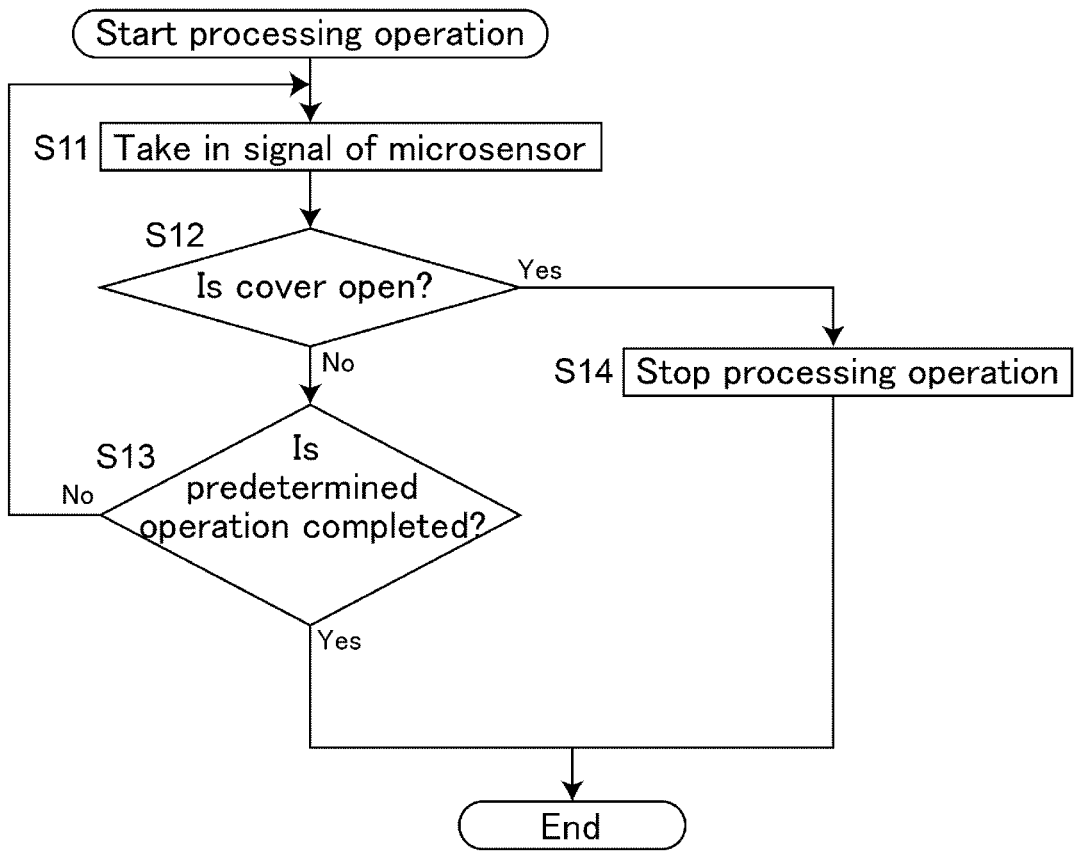
FIG. 5 is a flowchart for explaining operation during processing operation of the embodiment.

Next, operation after the processing operation is started will be described with reference to the flowchart of FIG. 5 together with FIG. 3.

During the execution of the processing operation, the control device 26 periodically receives a signal from the microsensor 22 (Step S11). The open/close state detector 30 checks the open/close state of the cover 16 based on the signal of the microsensor 22 (Step S12). In a case where the cover is closed, the operation controller 28 continues the operation until the predetermined processing operation is completed (Step S13). In contrast, in a case where the cover is opened, the operation controller 28 stops the driving of the stepping motor 14 and stops the processing operation being executed (Step S14).

DESCRIPTION OF REFERENCE SIGNS

1: Housing
2: Front panel
4: Recess
6: Opening
8: Magnetic force source
10: Holding block
12: Ball screw
14: Stepping motor
16: Cover
18: Pressing plate
20: Elastic member
22: Microsensor
24: Sensor dog
26: Control device
28: Operation controller
30: Open/close state detector
100: Tubular device
102: Sample layer
104: Treatment liquid layer
106: Eluate layer
108: Gel layer

The invention claimed is:

1. A magnetic particle manipulating apparatus comprising:
at least one device holder configured to hold a tubular device, wherein the tubular device includes a plurality of treatment liquid layers, which are each formed by treatment liquids for performing processing on a target substance and are layered in a longitudinal direction of the tubular device in a state where a gel layer interposed therebetween, and wherein a magnetic particle for capturing the target substance is provided in the tubular device;
a magnetic force source for manipulating the magnetic particle from outside of the tubular device by applying a magnetic force to the magnetic particle in the tubular device held by the at least one device holder;
a magnetic source moving mechanism that moves the magnetic source in a longitudinal direction of the tubular device at a position close to the tubular device held by the at least one device holder;
an operation controller configured to execute processing operation of moving the magnetic particle in the tubular device to each of the treatment liquid layers sequentially by controlling operation of the magnetic source moving mechanism;
an openable cover that covers the device holder;
a pressing plate attached to an inside surface of the cover by a plurality of elastic members and positioned so as to press the tubular device held by the device holder toward the magnetic force source when the cover is closed so that warpage of the tubular device is corrected; and
an open/close state detector provided so as to detect an open/close state of the cover,
wherein the operation controller is configured to execute the processing operation only in a case where the open/close state detector detects that the cover is closed.

2. The magnetic particle manipulating apparatus according to claim 1, wherein the operation controller is configured to stop the operation of the magnetic source moving mechanism to stop the processing operation when the open/close state detector detects that the cover is open while the processing operation is executed.

3. The magnetic particle manipulating apparatus according to claim 1, wherein the operation controller is configured not to execute the processing operation in a case where the open/close state detector detects that the cover is open at the time when an instruction to start the processing operation is input.

4. The magnetic particle manipulating apparatus according to claim 1, wherein two or more of the at least one device holders are provided.

\* \* \* \* \*